United States Patent [19]  [11] 4,031,110
Stockel et al.  [45] June 21, 1977

[54] METHOD OF PREPARING 3,3-BIS(CHLOROMETHYL) OXETANE

[75] Inventors: Richard Frederick Stockel, Bridgewater; Peter Carl Valenti, East Windsor, both of N.J.

[73] Assignee: National Patent Development Corporation, New York, N.Y.

[22] Filed: July 13, 1976

[21] Appl. No.: 704,887

[52] U.S. Cl. ................................................ 260/333
[51] Int. Cl.² ..................................... C07D 305/06
[58] Field of Search ........................... 260/333, 633

[56] References Cited
UNITED STATES PATENTS 2,794,027  5/1957  Schilling ............................ 260/333

FOREIGN PATENTS OR APPLICATIONS 765,531  1/1957  United Kingdom .............. 260/333

Primary Examiner—Norma S. Milestone

[57] ABSTRACT

3,3-bis (chloromethyl) oxetane is prepared by a method which comprises reacting N,N-dimethyl formamide with thionyl chloride to produce Vilsmeier reagent, followed by the reaction of the Vilsmeier reagent with pentaerythritol to produce pentaerythritol monochlorohydrin. The pentaerythritol monochlorohydrin is then reacted with thionyl chloride to produce pentaerythritol trichlorohydrin, followed by the reaction of pentaerythritol trichlorohydrin with an alkali metal hydroxide or an alkaline earth metal hydroxide to 3,3-bis (chloromethyl) oxetane.

14 Claims, No Drawings

METHOD OF PREPARING 3,3-BIS (CHLOROMETHYL) OXETANE

BACKGROUND OF INVENTION

1. Field of Invention

This invention relates to the preparation of 3,3-bis(-chloromethyl) oxetane and is particularly related to an improved process for the preparation of this compound in high yield, and in high degree of purity.

2. The Prior Art

It is well recognized in the prior art that 3,3-bis(-chloromethyl) oxetane may be polymerized to commercially valuable polymers which can be formed into films or molded into various shaped objects. Several methods have heretofore been disclosed for the preparation of this monomer, i.e., 3,3-bis(chloromethyl) oxetane. According to one method which is described in U.S. Pat. No. 2,794,027, an aqueous dispersion of pentaerythritol trichloromonohydrin or an ester thereof, is contacted with an inorganic base such as an alkali metal hydroxide at a temperature of 90° to 170° c., and the resulting 3,3-bis(chloromethyl) oxetane is removed from the reaction mixture by distillation.

Another method of preparation of this monomer is described by F. J. Connelly in an article entitled "Case History of Polymer Process Development," published in Chem. Eng. Prog. Symosium Series, No. 49, vol. 60, pp. 49–57. The method described in this article contemplates a three step reaction process in which pentaerythritol is first acetylated with acetic acid to prepare pentaerythritol tetraacetate, followed by the hydrochlorination of said pentaerythritol tetraacetate to pentaerythritol trichloroacetate and, finally, reacting said pentaerythritol trichloroacetate with sodium hydroxide to produce 3,3-bis(chloromethyl) oxetane by a so-called "ring closure" reaction.

The process described in the foregoing article suffers from disadvantages in that low yields and/or low degrees of purity of 3,3-bis(chloromethyl) oxetane product are produced which product is not particularly well suited as polymerization grade monomer. In addition, and in some instances, the production of 3,3-bis(-chloromethyl) oxetane, or its precursors, is accompanied by the production of considerable amounts of undersirable by-products which extremely complicate the production and recovery of the desired monomer, hence making it economically unfeasible to operate the process on a commercial scale. There is thus a need for an efficient, commercially practicable method of making 3,3-bis (chloromethyl) oxetane in substantial yield and in high degree of purity.

SUMMARY OF THE INVENTION

In its broad aspect, the present invention comprises reacting N,N-dimethyl formamide and thionyl chloride to produce the so-called "Vilsmeier" reagent, followed by the reaction of the Vilsmeir reagent with pentaerythritol to produce pentaerythritol monochlorohydrin, which is, in turn, reacted with thionyl chloride to produce pentaerythritol trichlorohydrin. The pentaerythritol trichlorohydrin is then reacted with an alkali metal hydroxide or an alkaline earth metal hydroxide under reflux conditions to produce 3,3-bis(-chloromethyl) oxetane which is desirably removed from the reaction mixture by steam distillation.

DETAILED DESCRIPTION OF THE INVENTION

In accordance with this invention, it has been unexpectedly discovered that polymerization grade 3,3-bis (chloromethyl) oxetane can be prepared in substantial yields, and in high degree of purity, by a unique method which comprises a series of reaction steps carried out under carefully controlled conditions designed to minimize the formation of undesirable by-products which would otherwise detract from the yield and/or purity of the desired product. Additionally, the process of this invention provides an efficient, commercially practicable method of producing 3,3-bis(chloromethyl) oxetane using well known and commercially available materials and equipment.

The novel method of this invention comprises four basic sequential steps, i.e., (1) preparation of the Vilsmeier reagent by the reaction of thionyl chloride and dimethyl formamide, (2) reaction of Vilsmeier reagent with pentaerythritol to produce pentaerythritol monochlorohydrin, (3) reaction of pentaerythritol monochlorohydrin with thionyl chloride to prepare pentaerythritol trichlorohydrin, and (4) reacting pentaerythritol trichlorohydrin with an alkali metal hydroxide or an alkaline earth metal hydroxide under reflux conditions to produce 3,3-bis(chloromethyl) oxetane, which is separated from the reaction products by distillation. It has been specifically discovered that the 3,3-bis(-chloromethyl) oxetane can be produced in high yield, and in high degree of purity, when step (3) supra, is carried out under conditions which minimize the formation of pentaerythritol monochlorohydrin and pentaerythritol dichlorohydrin.

The following example will serve to illustrate the process of this invention, it being clearly understood, however, that the conditions of the reactions described therein are by no means intended to limit the scope of this invention.

EXAMPLE

A 500 ml. three-necked flask was equipped with a mechanical stirrer, reflux condenser, thermometer, dropping funnel and an electric heating mantle. Dimethyl formamide [57.2 ml. (54 grams)] was charged to the flask under agitation, and [54 ml. (87 grams)] of thionyl chloride was introduced, dropwise, into the flask over a 5-minute period under continuous agitation while the solution temperature rose to 55° C. Stirring was continued for an additional 1-hour period during which time the temperature of the solution dropped to 30° C. The resulting solution (Vilsmeier reagent) weighed approximately 141 grams.

Thereafter, 100 grams solid pentaerythritol was added to the resulting solution over a 15-minute period. The pentaerythritol was added slowly due to rapid evolution of gas which is formed during this reaction and the temperature of the solution reached 60° C. during this period. The solution was then slowly heated to 120° C. over an additional 90-minute period, by which time the gas evolution had essentially ceased.

Thionyl chloride [116.3 ml. (188 grams)] was then added to the resulting mixture over a 3-hour period while the temperature was maintained between 120° and 125° C. After complete addition of the thionyl chloride, the reaction mixture was stirred for an additional 6 hours and then allowed to cool to about 80° C. Thereafter, [250 ml. (335 grams)] of 12 M sodium hydroxide was added to the cooled reaction mixture, the first 50 ml. being added slowly due to the exothermic nature of the reaction. The resulting solution was then stirred under reflux conditions for 3 hours. The reaction mixture measured approximately 400 ml. (520 grams). This mixture was then steam distilled in order to separate the 3,3-bis(chloromethyl) oxetane as the bottoms. The distillate (approximately 945 grams) was extracted with 134 grams of methylene chloride in a Scheibel extraction column at a temperature of 25° C. and the extract was combined with the distillation bottoms. The resulting combined solution was dried over 15 grams of sodium sulfate and the methylene chloride was removed by flash evaporation to yield 87 grams of products which consisted of 77 percent by weight 3,3-bis(chloromethyl) oxetane and 23 percent by weight pentaerythritol tetrachloride. The latter may be separated by vacuum fractional distillation to yield substantially pure 3,3-bis(chloromethyl) oxetane.

The yield of 3,3-bis(chloromethyl) oxetane based on pentaerythritol in the foregoing example was 59 percent.

As it was previously mentioned, the conditions of the various reaction steps of the process of this invention are not necessarily limited to those described in the foregoing example, but may be varied over a relatively wide range. For example, the Vilsmeier reaction may be carried out at a temperature of from about 15° C., or somewhat lower, to about 125° C., or somewhat higher, preferably from about 40° to about 70° C., using N,N-dimethyl formamide and thionyl chloride in a molar ratio of from about 0.5 to about 3 moles of N,N-dimethyl formamide and from about 0.5 to about 3 moles of thionyl chloride, preferably about 0.75 to about 1.25 moles of N,N-dimethyl formamide and about 0.75 to about 1.25 thionyl chloride.

The Vilsmeier reagent may, if desired, be prepared using other N,N-disubstituted formamides such as N,N-dialkyl formamide wherein the alkyl group contains 1 to 4 carbon atoms, and utilizing other chlorinating agents such as $POCl_3$ or $COCl_3$ although N,N-dimethyl formamide and thionyl chloride are most preferable for the purpose of this invention.

The reaction of the Vilsmeier reagent with pentaerythritol to produce pentaerythritol monochlorohydrin may be carried out at a temperature of from about 15° C., or somewhat lower, to about 125° C., or somewhat higher, preferably from about 30° to about 60° C., using from about 0.5 to about 3 moles of the Vilsmeier reagent and from about 0.8 to about 1.2 moles of pentaerythritol, preferably from about 0.75 to about 1.25 moles of Vilsmeier reagent and from about 0.95 and about 1.05 moles of pentaerythritol.

As it was previously mentioned, the reaction of pentaerythritol monochlorochydrin with thionyl chloride to produce pentaerythritol trichlorhydrin is critical in the process of this invention, and must be carried out under conditions which minimize the formation of pentaerythritol monochlorohydrin and pentaerythritol dichlorohydrin. The presence of these reaction by-products complicates product recovery and adversely affects the yield and/or purity of 3,3-bis(chloromethyl) oxetane. Thus, this reaction is most advantageously carried out at a temperature of from about 90° to about 125° C., for a period of from about 9 hours to about 24 hours, using from about 0.8 to 1.2 moles of pentaerythritol monochlorohydrin and from about 1.4 to about 2.6 moles of thionyl chloride, preferably from about 0.95 to about 1.05 moles of pentaerythritol monochlorohydrin to and about 1.8 to about 2.2 moles of thionyl chloride.

The last reaction, i.e., the reaction of pentaerythritol trichlorohydrin with an alkali metal hydroxide or an alkaline earth metal hydroxide is carried out under moderately elevated temperature, e.g., from about 50° C., and somewhat lower, to the reflux temperature of the reaction mixture, and desirably under refluxing conditions, using from about 0.8 to about 1.2 moles of pentaerythritol trichlorohydrin and 0.8 to 10 moles of the base, preferably from about 0.95 to about 1.05 moles of pentaerythritol trichlorohydrin and about 2.5 to about 6 moles of the hydroxide.

The alkali metal hydroxides and alkaline earth metal hydroxides that can be used in the last reaction are described in U.S. Pat. No. 2,794,027, supra.

In the foregoing reactions, pressure, per se, is not critical. Suffice it to indicate that the rates of reactions 1, 2 and 3 are generally enhanced at lower pressures, and reduced as the pressure is increased, whereas reaction 4 is substantially unaffected by pressure.

The process of this invention may be carried out continuously, semi-continuously or in batchwise fashion, using commercially available equipment and materials. Also, as it may well be appreciated by those skilled in the art, many obvious variations and modifications may be made in the process of this invention which are nevertheless obvious from the disclosure herein and thus fall within the scope of this invention.

What is claimed is:

1. A process for making 3,3-bis(chloromethyl) oxetane which comprises:
   a. reacting N,N-dialkyl formamide, wherein the alkyl group contains from 1 to 4 carbon atoms, with a chlorinating agent selected from the group consisting of $SOCl_2$, $POCl_3$, and $COCl_2$, at a temperature of from about 15° to about 125° C.,
   b. reacting the product obtained from step (a) with pentaerythritol at a temperature of from about 15° C. to about 125° C. to make pentaerythritol monochlorohydrin,
   c. reacting said pentaerythritol monochlorohydrin with $SOCl_2$ to form pentaerythritol trichlorohydrin under conditions which substantially minimize the formation of pentaerythritol monochlorohydrin and pentaerythritol dichlorohydrin,
   d. reacting said pentaerythritol trichlorohydrin with a metal hydroxide selected from the group consisting of alkali metal hydroxides and alkaline earth metal hydroxides at a temperature in the range of from about 50° C. to the reflux temperature of the reaction mixture, to produce 3,3-bis(chloromethyl)oxetane, and
   e. removing said 3,3-bis(chloromethyl)oxetane from the reaction mixture.

2. The process of claim 1 wherein said N,N-dialkyl formamide is N,N-dimethyl formamide.

3. The process of claim 1 wherein said chlorinating agent is thionyl chloride.

4. The process of claim 1 wherein said N,N-dialkyl formamide is N,N-dimethyl formamide and wherein said chlorinating agent is thionyl chloride.

5. The process of claim 4 wherein reaction (c) is carried out at a temperature of from about 90° to about 125° C. for a period of from about 9 hours to about 24 hours.

6. The process of claim 5 wherein from about 0.5 to about 3 moles of thionyl chloride and from about 0.5 to about 3 moles of N,N-dimethyl formamide are used in reaction (a), from about 0.5 to about 3 moles of product of reaction (a) and from about 0.8 to about 1.2 moles of pentaerythritol are used in reaction (b), from about 0.8 to about 1.2 moles of pentaerythritol monochlorohydrin and from about 1.4 to about 2.6 moles of thionyl chloride are used in reaction (c) and from about 0.8 to about 1.2 moles of pentaerythritol trichlorohydrin and from about 0.8 to about 10 moles of said metal hydroxide are used in reaction (d).

7. The process of claim 6 wherein said 3,3-bis(-chloromethyl) oxetane is removed from products of reaction (d) by vacuums fractional distillation.

8. The process of claim 5 wherein said metal hydroxide is sodium hydroxide.

9. The process of claim 6 wherein said metal hydroxide is sodium hydroxide.

10. The process of claim 7 wherein said metal hydroxide is sodium hydroxide.

11. The process of claim 5 wherein from about 0.75 to about 1.25 moles of thionyl chloride and from about 0.75 to about 1.25 moles of N,N-dimethyl formamide are used in reaction (a), from about 0.75 to about 1.25 moles of product of reaction (a) and from about 0.95 to about 1.05 moles of pentaerythritol are used in reaction (b), from about 0.95 to about 1.05 moles of pentaerythritol monochlorohydrin and from about 1.8 to about 2.2 moles of thionyl chloride are used reaction (c) and from about 0.95 to about 1.05 moles of pentaerythritol trichlorohydrin and from about 2.5 to about 6 moles of said metal hydroxide are used in reaction (d).

12. The process of claim 11 wherein said 3,3-bis(-chloromethyl) oxetane is removed from the products of reaction (d) by vacuum fractional distillation.

13. The process of claim 11 wherein said metal hydroxide is sodium hydroxide.

14. The process of claim 12 where said metal hydroxide is sodium hydroxide.

* * * * *